United States Patent

Osypka

Patent Number: 5,251,643
Date of Patent: Oct. 12, 1993

[54] MULTIPOLAR CARDIAC PACEMAKER LEAD

[76] Inventor: Peter Osypka, Basler Strasse 109, D-7889 Grenzach-Wyhlen, Fed. Rep. of Germany

[21] Appl. No.: 794,871
[22] Filed: Nov. 19, 1991

[30] Foreign Application Priority Data

Dec. 22, 1990 [EP] European Pat. Off. ............ 90125337

[51] Int. Cl.⁵ .............................................. A61N 1/05
[52] U.S. Cl. .................................................... 607/122
[58] Field of Search ............... 128/419 P, 784, 785, 128/786, 642

[56] References Cited

U.S. PATENT DOCUMENTS

| | | | |
|---|---|---|---|
| 4,387,727 | 6/1983 | Sandstrom | 128/784 |
| 4,590,950 | 5/1986 | Iwaszkiewicz | 128/786 |
| 4,608,986 | 9/1986 | Beranek et al. | 128/786 |
| 4,628,943 | 12/1986 | Miller | 128/785 |

FOREIGN PATENT DOCUMENTS 0292596 11/1988 European Pat. Off. .
3043189 7/1984 Fed. Rep. of Germany .
3640033 5/1988 Fed. Rep. of Germany .
3718324 12/1988 Fed. Rep. of Germany .
8119037 4/1982 France .

Primary Examiner—William E. Kamm
Assistant Examiner—Scott M. Getzow
Attorney, Agent, or Firm—Peter K. Kontler

[57] ABSTRACT

A multipolar cardiac pacemaker lead wherein the distal end carries a first electrode and at least one sleeve-like additional electrode is provided between the first electrode and the proximal end. Each additional electrode is positively connected with a corresponding helically wound wire-like conductor of the lead by a tubular conductor within an insulating sheath of the lead and by one or more flexible metallic bands each of which has a distal portion soldered or welded to the internal surface of the respective additional electrode, a second portion soldered or welded to the respective tubular conductor, and an S-shaped or Z-shaped intermediate portion extending between and contacting the adjacent convolutions of the respective wire-like conductor. Each tubular conductor is welded or soldered to at least one adjacent convolution of the corresponding wire-like conductor. The wire-like conductors are electrically insulated from each other.

21 Claims, 3 Drawing Sheets

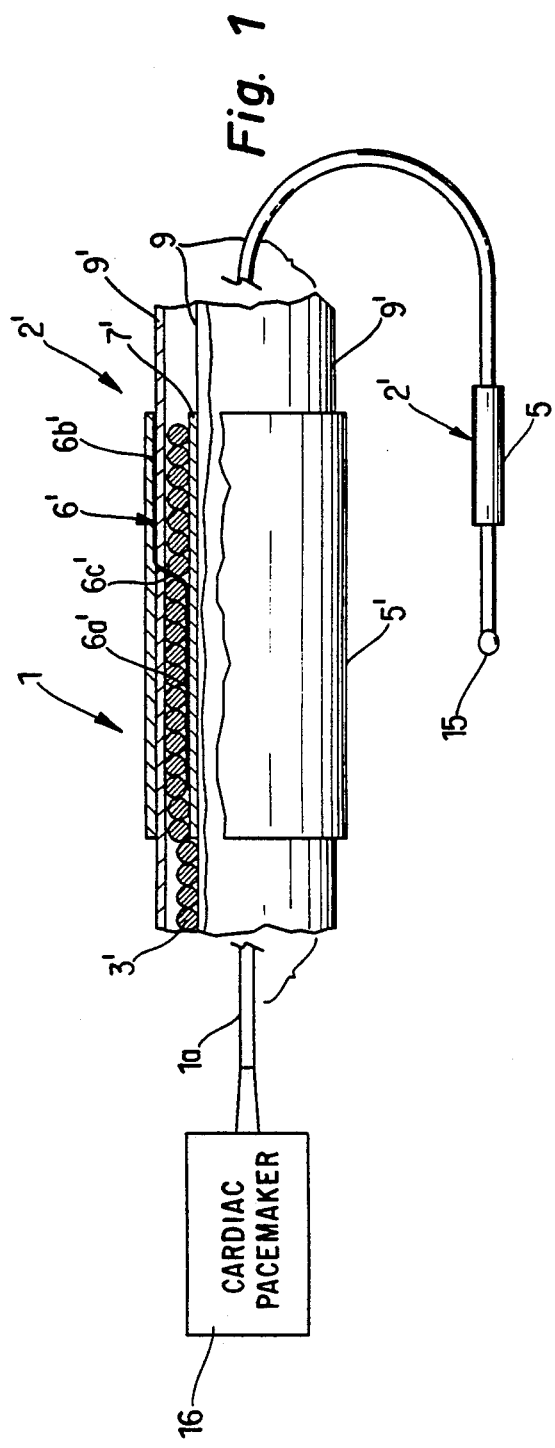
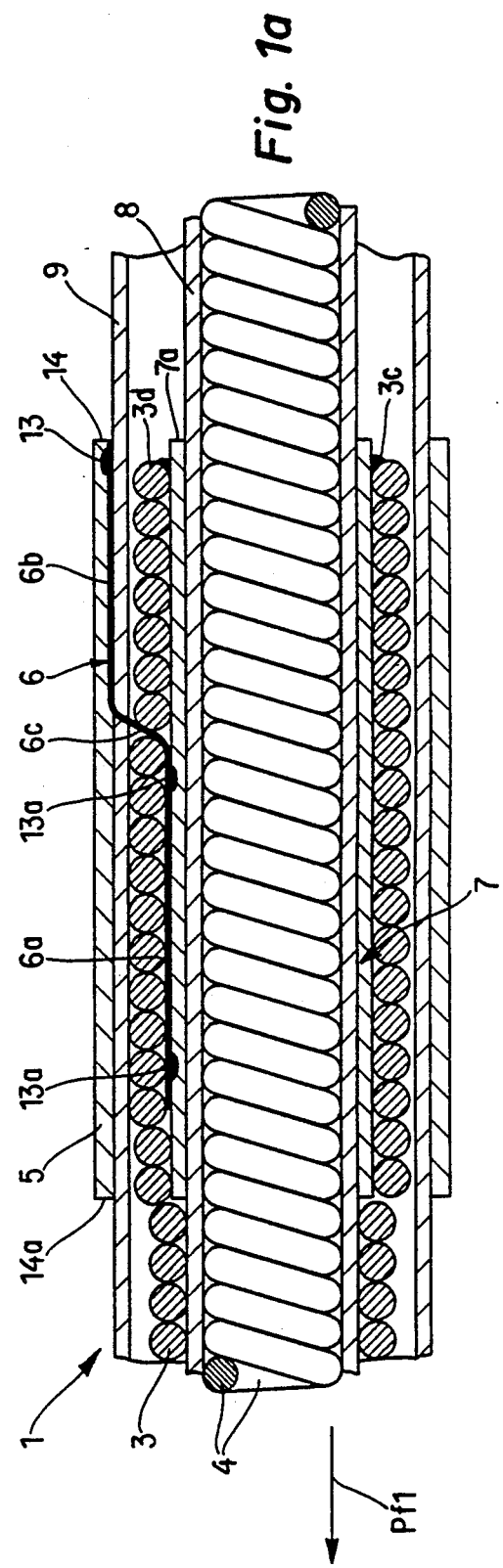

MULTIPOLAR CARDIAC PACEMAKER LEAD

BACKGROUND OF THE INVENTION

The invention relates to cardiac pacemaker leads in general, and more particularly to improvements in multipolar cardiac pacemaker leads.

U.S. Pat. No. 4,590,950 granted May 27, 1986 to Iwaszkiewicz et al. discloses a bipolar cardiac pacemaker lead wherein a distal electrode tip is located a specified distance away from an indifferent ring electrode. Each of the two electrodes is connected to a discrete conductor in the form of helically wound wire, and the ring electrode is dimensioned in such a way that its outer diameter matches the outer diameter of a sleeve-like insulator for the helically wound wires. The ring electrode is not positively connected to any other part but is merely a press fit on the insulator. One or more bridging wires are used to establish an electrical connection between the ring electrode and the corresponding helically wound wire, and each bridging wire extends through the sleeve-like insulator. The absence of positive connections between the bridging wires and the parts which are in electric contact therewith renders it possible to extract the helically wound wire or wires and thus render the lead useless for its intended purpose.

German Pat. No. 30 43 189 C3 granted Jul. 12, 1984 to Osypka discloses a cardiac pacemaker lead wherein the proximal pacing electrode is a sleeve. The terminal or terminals of the corresponding helically wound wire are caused to pass through an insulating sleeve and are affixed to the sleeve-like electrode.

German patent application No. 37 18 324 A1 of Hirschberg (published Dec. 22, 1988) discloses a cardiac pacemaker lead which employs conductors having different diameters. The sleeve-like pacing electrode is slipped over the end portion of the larger-diameter conductor and directly engages such end portion because the corresponding portion of the sleeve-like insulator is removed together with insulation on the end portion of the larger-diameter conductor. This proposal exhibits the drawback that the utilization of conductor wires having different wire diameters as well as convolutions of different diameters contributes to the initial and assembly cost of the lead. The stability of the lead is unsatisfactory, partly due to movements of the heart in which the electrodes of the lead are implanted and partly due to the absence of positive electrical connections between the wires and the respective electrodes. Still further, the danger of short-circuiting the lead is ever present because the movements of the heart are likely to entail the establishment of electric contact between the smaller-diameter convolutions and the sleeve-like proximal electrode.

European patent application No. 0 292 596 A1 of Hirschberg (published Nov. 30, 1988) discloses a method of electrically connecting conductors and electrodes in an implantable electrode lead. The inventor proposes to employ a curved tool which serves to extract a portion of a conductor which is embedded in two insulating layers. The thus extracted portion of the conductor can be connected to a composite pacing electrode, namely an electrode having two coaxial sleeves which are turned relative to each other so that the extracted portion of the conductor is clamped between the internal surface of the outer sleeve and the external surface of the inner sleeve. Such proposal exhibits the drawback that the two sleeves of the electrode are likely to shear off the exposed portion of the conductor. Movements of the electrode upon implantation into the heart of a patient are likely to interrupt the electrical connection between the sheared off portion and the major portion of the electrode. Moreover, it is rather difficult or plain impossible to inspect the quality and reliability of the connection between the conductor and the electrode, especially in the regions where the exposed portion of the conductor is engaged by the edges of the inner sleeve of the electrode.

German patent application No. 36 40 033 A1 of Hirschberg (published May 26, 1988) discloses a cardiac pacemaker lead wherein the helically wound wires of the conductors are reinforced in that the neighboring convolutions of certain portions of such conductors are fixedly connected to each other. This results in undesirable stiffening of the lead which can create problems during implantation.

U.S Pat. No. 4,387,727 granted Jun. 14, 1983 to Sandstrom discloses a coaxial service kit which is used to splice body implantable bipolar leads of the type having coaxial inner and outer coil wire conductors. The patentee proposes to employ a conductive pin and a set screw.

U.S. Pat. No. 4,628,943 granted Dec. 16, 1986 to Miller discloses a bipolar screw-in pacing lead assembly wherein the proximal electrode is electrically connected to the respective helically wound wire-like conductor by a brush contact.

French patent application No. 81 19037 of Sandstrom et al. (published Apr. 15-16, 1982) discloses a cardiac pacemaker lead wherein a helically wound-wire-like conductor is surrounded by an insulating sheath and is in contact with several axially parallel internal conductors. A sleeve-like electrode is slipped onto the sheath so that it frictionally engages the internal conductors and the sheath.

OBJECTS OF THE INVENTION

An object of the invention is to provide a novel and improved multipolar cardiac pacemaker lead wherein the electrical connection or connections between the proximal pacing electrode or electrodes and the corresponding conductor or conductors is or are more reliable than in heretofore known leads.

Another object of the invention is to provide a novel and improved electrical connection between a helically wound wire-like conductor and a proximal pacing electrode in a multipolar cardiac pacemaker lead.

A further object of the invention is to provide a novel and improved method of assembling a multipolar cardiac pacemaker lead.

An additional object of the invention is to provide novel and improved means for reliably insulating the wire-like conductors of a multipolar cardiac pacemaker lead from each other and from selected pacing electrodes.

Still another object of the invention is to provide a novel and improved method of preventing accidental or unintentional separation of one or more helically wound wire-like conductors from the respective proximal electrode or electrodes in a multipolar cardiac pacemaker lead.

A further object of the invention is to provide a novel and improved bipolar cardiac pacemaker lead.

Another object of the invention is to provide a novel and improved tripolar cardiac pacemaker lead.

An additional object of the invention is to provide a novel and improved arrangement of helically wound wire-like conductors in a cardiac pacemaker lead of the above outlined character.

A further object of the invention is to provide a novel and improved arrangement for reinforcing one or more selected portions of a multipolar cardiac pacemaker lead.

Another object of the invention is to provide a multipolar cardiac pacemaker lead wherein the conductors can stand more pronounced tensional stresses than in heretofore known leads.

Still another object of the invention is to provide a multipolar cardiac pacemaker lead which can stand pronounced dynamic stresses without damage to the electrical connections between its pacing electrodes and the respective conductors.

SUMMARY OF THE INVENTION

The invention is embodied in a cardiac pacemaker lead having a proximal end and a distal end and comprising a first pacing electrode at the distal end, a preferably tubular second pacing electrode between the first electrode and the proximal end, a first elongated conductor connected to the first electrode and extending toward the proximal end, a second elongated conductor insulated from the first conductor and extending from the second electrode toward the proximal end, at least one substantially band-shaped third conductor, and means for positively connecting (particularly welding or soldering) the at least one third conductor to the second conductor and/or to the second electrode. The lead further comprises a tubular insulator which surrounds the first and second conductors and is surrounded by the second electrode. At least one of the first and second conductors can constitute a helically wound wire with neighboring convolutions.

The connecting means can comprise a tubular fourth conductor which is surrounded by or surrounds the second conductor and is preferably positively connected with the at least one third conductor. The at least one third conductor can include a first elongated portion which contacts the second electrode, a second elongated portion which contacts the fourth electrode, and a substantially Z-shaped or S-shaped intermediate portion between the first and second portions. At least one of the first and second portions of the at least one third conductor preferably extends at least substantially axially of the second electrode and of the fourth conductor. The length of the fourth conductor can equal or approximate (namely exceed or be less than) the length of the second electrode.

The second electrode can be a press fit on the tubular insulator, e.g., in such a way that its external surface does not project radially outwardly beyond the neighboring non-surrounded portions of the tubular insulator.

The arrangement may be such that each of the first and second conductors is a helically wound wire and the second conductor coaxially surrounds the first conductor. Such lead can further comprise a second tubular insulator which surrounds the first conductor and is surrounded by the second conductor. The tubular fourth conductor can be disposed between the second insulator and the second conductor. The first portion of the at least one third conductor is preferably connected to the internal surface of the second electrode, the second portion of the at least one third conductor contacts the fourth conductor and the intermediate portion of the at least one third conductor preferably extends transversely of and through the second conductor and the first mentioned tubular insulator. Such intermediate portion can contact one, two or more convolutions of the second conductor.

If each of the first and second conductors comprises a helically wound wire with neighboring convolutions, the two wires can have a common axis and such wires are insulated from each other and have, or can have, at least substantially identical outer diameters. The fourth conductor can be confined in the first and second conductors. The first portion of the at least one third conductor can be electrically connected to the internal surface of the second electrode, and the intermediate portion of the at least one third conductor then extends between the convolutions of the second and/or first conductor. The second tubular insulator (between the fourth conductor and the helically wound wires of the first and second conductors) has an opening for an end portion of the second conductor so that such end portion can be connected to the fourth conductor. The intermediate portion of the at least one third conductor then extends through the second insulator and between the convolutions of the first and/or second conductor. The first portion of the at least one third conductor can be connected to the internal surface of the second electrode, the second portion of the at least one third conductor can be connected to the fourth conductor, and the intermediate portion of the at least one third conductor then extends through the second insulator and between the convolutions of the second and/or first conductor. The first portion of the at least one third conductor is connected to the internal surface of the second electrode.

If the tubular fourth conductor surrounds the helically wound wires of the first and second conductors and is surrounded by the second electrode, the first tubular insulator surrounds the wires and is surrounded by the fourth conductor, and the second tubular insulator is disposed between the second electrode and the fourth conductor. The end portion of the second conductor extends through the first insulator and is connected to the external surface of the fourth conductor, and the at least one third conductor is connected to the external surface of the fourth conductor and extends through the second insulator to the internal surface of the second electrode.

The connecting means between the at least one third conductor and the second electrode and/or between the at least one third conductor and the fourth conductor preferably includes a welded or soldered joint. The connection between the at least one third conductor and the second electrode can comprise one or more welded or soldered joints at least one of which is preferably adjacent that axial end of the second electrode which is nearer to the first electrode. The end portion of the second conductor can be welded or soldered to the fourth conductor.

The lead can further comprise a third tubular electrode which is adjacent the second electrode (either between the first and second electrodes or between the second electrode and the proximal end of the lead), a further conductor which extends from the third electrode toward the proximal end of the lead, and means for electrically connecting the further conductor with the third electrode. The means for electrically connecting the further conductor with the third electrode can comprise a tubular conductor which is surrounded by the third electrode and is connected with the further conductor by at least one substantially band-like conductor which connects the tubular conductor with the third electrode.

The novel features which are considered as characteristic of the invention are set forth in particular in the appended claims. The improved multipolar lead itself, however, both as to its construction and the mode of assembling the same, together with additional features and advantages thereof, will be best understood upon perusal of the following detailed description of certain presently preferred specific embodiments with reference to the accompanying drawing.

BRIEF DESCRIPTION OF THE DRAWING

FIG. 1 is a somewhat schematic partly elevational and partly sectional view of a tripolar cardiac pacemaker lead which embodies one form of the present invention, different sections of the lead being drawn to different scales;

FIG. 1a is an enlarged axial sectional view of the lead at the location of the second pacing electrode or pole;

FIG. 2 shows a first stage of assembly of the structure which is shown in FIG. 1a;

FIG. 3 shows a second stage of assembly of the structure which is shown in FIG. 1a;

FIG. 4 shows a third stage of assembly of the structure which is shown in FIG. 1a;

DESCRIPTION OF PREFERRED EMBODIMENTS

Figure 2:
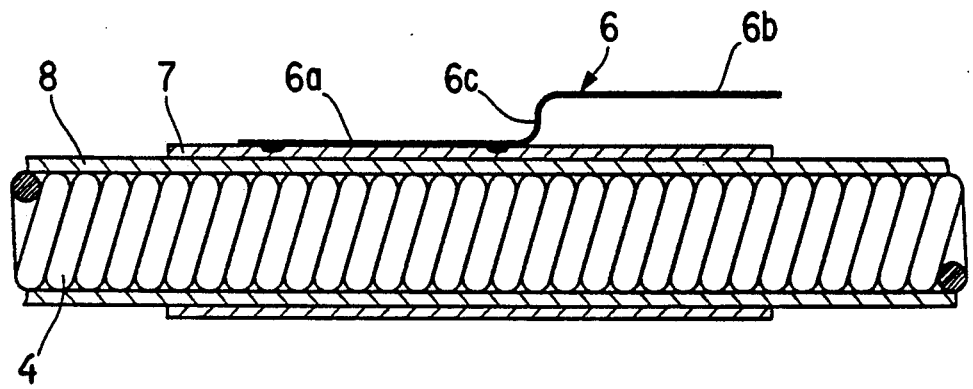

Referring first to FIG. 1, there is shown a tripolar cardiac pacemaker lead 1 having a proximal end 1a connected to a pacemaker 16, a first pacing electrode or pole 15 at the distal end 1b, a tubular or sleeve-like second pacing electrode or pole 5 (FIG. 1a) at a location 2 between the electrode 15 and the proximal end 1a, and a third sleeve-like or tubular pacing electrode or pole 5' at a location 2' between the electrode 5 and the proximal end 1a.

FIGS. 1a, 2, 3 and 4 illustrate the structure at the location 2, namely the manner in which the electrode 5 is electrically connected with a (second) helically wound wire-like conductor 3. Another (first) helically wound wire-like conductor 4 has a distal end which is connected to the first electrode 15 and this conductor extends toward the proximal end 1a, the same as the conductor 3. The lead 1 further comprises a first tubular sheath-like insulator 9 which surrounds the convolutions of the conductor 3 and extends (or can extend) all the way to the electrode 15, and a second tubular sheath-like insulator 8 which is disposed between the conductors 3, 4 and also extends (or can extend) all the way to the electrode 15. The means for electrically connecting the electrode 5 to the adjacent distal end portion of the second conductor 3 comprises one or more elongated band- or strip-shaped third conductors 6 (only one shown), a tubular fourth conductor 7 which is confined between the convolutions of the conductor 3 and the second insulator 8, one or more first soldered or welded joints 13 (only one shown) which positively connect a first or distal portion 6b of the illustrated third conductor 6 (hereinafter called band for short) to the electrode 5, and one or more soldered or welded joints 13a (two shown) which connect the tubular conductor 7 with a proximal second portion 6a of the band 6. A Z-shaped or S-shaped intermediate portion 6c between the portions 6a, 6b of the band 6 extends between and contacts at least two neighboring convolutions of the second conductor 3. The distal end 7a of the conductor 7 is welded or soldered to the adjacent end convolution 3d of the conductor 3, and the electrode 5 has a first or proximal end 14a and a second or distal end 14 which latter is adjacent the welded or soldered joint 13.

The electrode 5 is or can be a tight press fit on the adjacent portion of the first insulator 9; in fact, the outer diameter of the electrode 5 can be selected in such a way that it does not exceed the outer diameters of adjacent exposed portions of the insulator 9. It will be noted that the first portion 6b of the band 6 is adjacent the internal surface of the electrode 5 and that the second portion 6a of the band 6 is adjacent the external surface of the tubular fourth conductor 7. The latter not only forms part of the means for positively connecting the distal end portion of the conductor 3 with the electrode 5 but it also reinforces or stiffens the lead 1 at the location 2, for example, to prevent excessive deformation of the electrical connection by the second electrode 5.

The portion 6a and/or the portion 6b of the band 6 preferably extends in substantial parallelism with the common axis of the electrode 5, conductor 7 and helically wound wire-like conductors 3, 4. The purpose of the intermediate portion 6c of the band 6 is to compensate for the difference between the inner diameter of the electrode 5 and the outer diameter of the conductor 7. If the conductor 3 is subjected to a pull in the direction of arrow Pfl, the electrical connection between the conductor 3 and the corresponding electrode 5 is apt to improve because the intermediate portion 6c of the band 6 is likely to bear against the adjacent convolutions of the conductor 3 with a progressively increasing force. A welded or soldered joint 3c prevents separation of the conductors 3, 7, the joint 13 prevents separation of the band portion 6b from the electrode 5, and the joints 13a prevent separation of the band portion 6a from the conductor 7.

The described positive connection between the conductor 3 and the electrode 5 is highly reliable because the conductor 7 is in direct frictional contact with the adjacent convolutions of the conductor 3 and the conductor 3 is also welded or soldered to the conductor 7 (as at 3a), the band 6 is welded or soldered to the conductor 6a (as at 13a), the band 6 is welded or soldered to the electrode 5 (as at 13) and the band 6 contacts several convolutions of the conductor 3 (as at 6c). Thus, the electrical connection between the electrode 5 and the conductor 3 does not rely primarily or exclusively on frictional and/or clamping engagement between the electrode 5 and the conductor 3 and/or on frictional and/or clamping engagement between the conductor 3 and the conductor 7 but is established by resorting to positive connections between the conductors 3, 7 between the band 6 and the conductor 7 and between the band 6 and the electrode 5.

The axial length of the conductor 7 can match or at least approximate the axial length of the electrode 5. It is equally within the purview of the invention to employ a conductor 7 which is shorter or longer than the electrode 5. The conductor 7 performs the aforediscussed dual purpose of (a) forming part of the positive electrical connection between the conductor 3 and the electrode 5 and (b) of reinforcing the location 2 of the electrode 5 and distal end portion of the conductor 3.

An advantage of the tubular sheath-like insulator 8 is that it is not necessary to provide the wire-like conductor 3 and/or 4 with its own insulating cover or sheath, i.e., each of the conductors 3, 4 can constitute a length of helically wound bare (uninsulated) wire.

Figure 3:
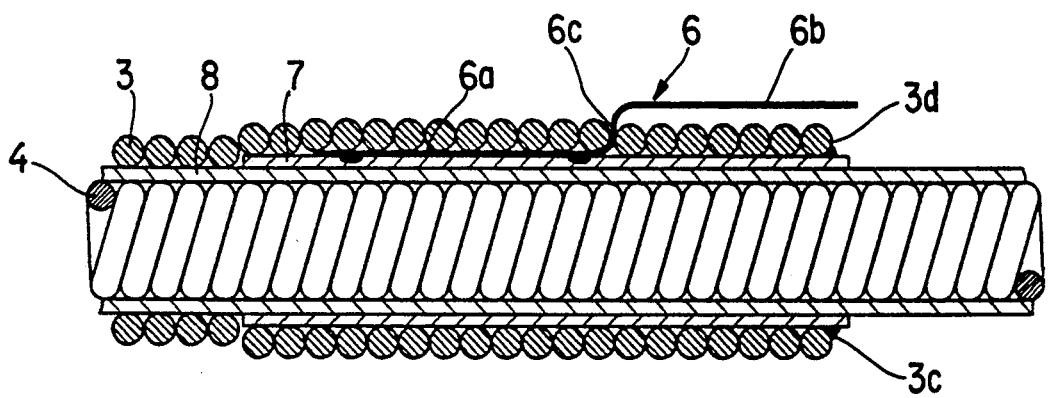
Figure 4:
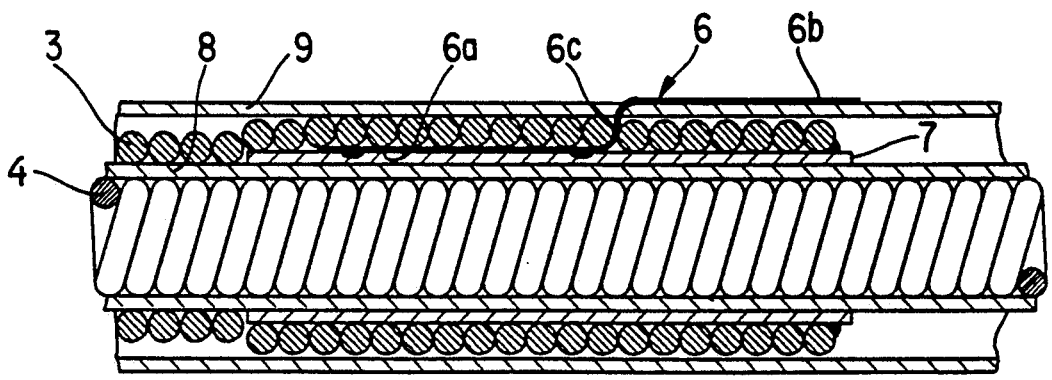

A presently preferred mode of establishing the afore-described positive electrical connection between the conductor 3 and the electrode 5 is shown in FIGS. 2, 3 and 4. FIG. 2 illustrates the stage following confinement of the conductor 4 in the insulator 8, application of the conductor 7 over the insulator 8, and welding or soldering of the band portion 6a to the external surface of the conductor 7. The next stage is shown in FIG. 3, i.e., the conductor 4 is already convoluted around the insulator 8, around the band portion 6a and around the conductor 7, the distal convolution 3d of the conductor 3 is welded or soldered (at 3c) to the conductor 7, and the intermediate portion 6c of the band 6 extends between two neighboring convolutions of the conductor 3. A further stage is shown in FIG. 4, i.e., the insulator 9 is slipped over the conductor 7, the intermediate portion 6c of the band 6 extends through the insulator 9, and the portion 6b of the band 6 overlies the external surface of the insulator 9. The last stage involves the application of the electrode 5 over the insulator 9 and bonding (at 13) of the distal end 14 of the electrode 5 to the distal portion 6b of the band 6 in order to arrive at the structure which is shown in FIG. 1a.

In addition to contributing to reliability of the electrical connection between the conductor 3 and the electrode or pole 5, and in addition to reinforcing the location 2 (particularly for the purpose of ensuring predictable and convenient application of the electrode 5 over the insulator 9), the conductor 7 can perform the desirable and advantageous function of biasing the band portion 6a against the adjacent (preferably bare) convolutions of the conductor 3 to thereby further enhance the reliability of the electrical connection between the parts 3 and 5. Furthermore, the conductor 7 bears against the band portion 6a as well as against those convolutions of the conductor 3 which are located between the band portion 6c and the joint 3c to thus even further reduce the likelihood of interruption of an electrical connection between the electrode 5 and the conductor 3 when the lead 1 is in actual use.

The electrical connection between the third pacing electrode 5' and a further helically wound wire-like conductor 3' of FIG. 1 is analogous to that which is shown in FIG. 1. This connection comprises a tubular conductor 7' which is disposed between the conductor 3' and the insulator 9, and at least one band 6' which is welded or soldered to the conductor 7' and electrode 5' and extends between two neighboring convolutions of the conductor 3' as well as through an outer sheath-like tubular insulator 9' which is disposed between the conductor and the electrode 5'. The latter is located between the electrode 5 and the proximal end 1a of the lead 1.

It is clear that the electrode 5' can be transposed between the electrodes 5 and 15; this would merely involve mounting of the insulator 9, and further conductor 3' between the insulator 8 and the conductor 3. Furthermore, the lead 1 can comprise, or can be replaced with, a lead having more than three electrodes, for example, one including the first or distal electrode 15, the electrodes 5, 5' and a further electrode between the electrodes 5, 15 or 5, 5' or between the electrode 5' and the proximal end 1a.

Figure 5:
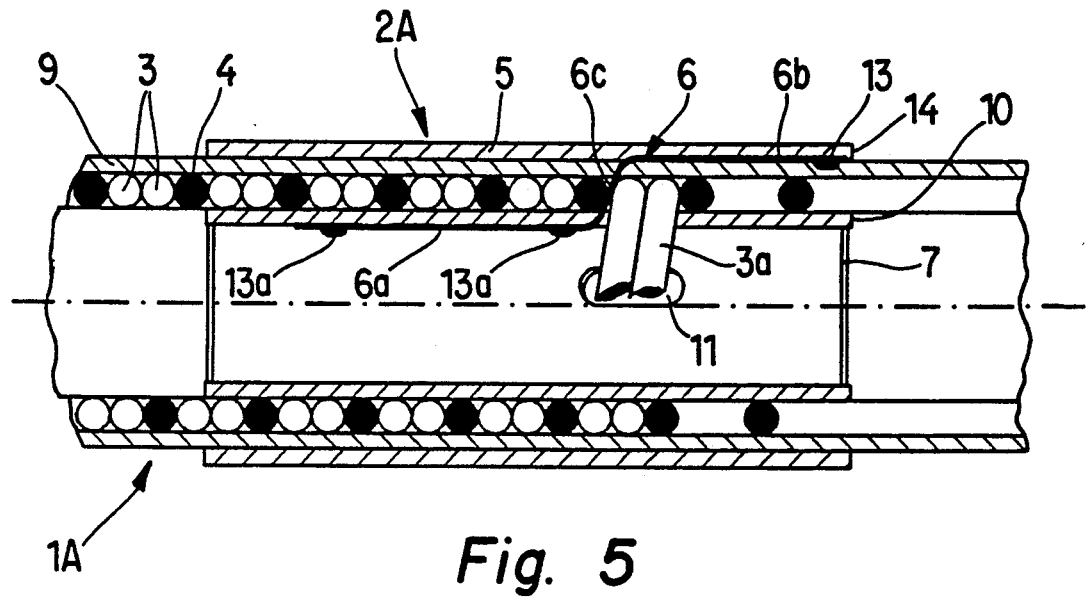
FIG. 5 is a sectional view similar to that of FIG. 1a but showing a portion of a different connection between a second pacing electrode or pole and the corresponding helical wire-like conductor.

FIG. 5 shows a location 2A where a cardiac pacemaker lead 1A is provided with a modified electrical connection between the (second) helical wire-like conductor 3 and the tubular sleeve-like pacing electrode 5. The conductors 3, 4 have a common axis (the same as in the embodiment of FIGS. 1 to 4) and their convolutions alternate and have identical or practically identical inner and outer diameters. The tubular fourth conductor 7 is confined in the conductors 3, 4 and is surrounded by a tubular insulator 10 which contacts the innermost portions of adjacent convolutions of the conductors 3 and 4. The distal end portion 3a of the conductor 3 extends through an opening 11 of the insulator 10 and is welded or soldered to the external surface of the conductor 7. The connection of FIG. 4 also comprises one or more band-like (third) conductors 6 (only one shown) each of which has a first portion 6b welded or soldered (at 13) to the internal surface of the electrode 5, a second portion 6a welded or soldered (at 13a) to the external surface of the conductor 7, and an S-shaped or Z-shaped intermediate portion 6c which extends through the insulators 10, 9 and contacts the end portion 3a of the conductor 3. The latter is electrically insulated from the conductor 4, e.g., in that the convolutions of the conductor 4 are provided with a layer of insulating material.

The conductor 3 extends beyond the insulator 10 and beyond the conductor 7 and is electrically connected with the distal or first pacing electrode 15 (not shown in FIG. 5).

The end portion 3a of the conductor 3 is bare (for example, the entire conductor 3 can consist of bare wire if the conductor 4 is provided with an insulating layer) so that such end portion can be readily welded or soldered to the adjacent portion of the conductor 7 radially inwardly of the opening 11 in the insulator 10. It is clear that the intermediate portion 6c of the band 6 is insulated from the conductor 4.

The insulation around the wire of the conductor 4 replaces the insulator 8 of FIGS. 1a to 4.

That portion of the insulator 10 which surrounds the band portion 6a ensures that this band portion is reliably insulated from the surrounding convolutions of the conductor 4. In other words, the insulator 10 insulates the conductor 4 from that portion (6a) of the band 6 which contacts the tubular conductor 7.

Figure 6:
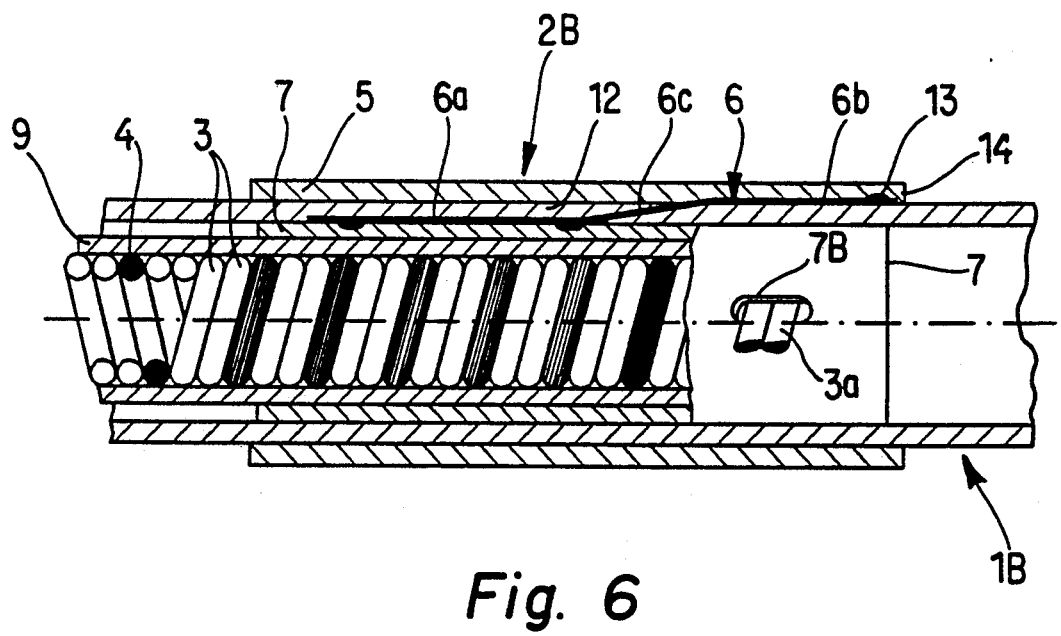
FIG. 6 is a sectional view similar to that of FIG. 5 but showing a portion of still another connection between a second pacing electrode or pole and the corresponding conductor.

FIG. 6 illustrates a further electrical connection which is utilized in a cardiac pacemaker lead 1B at a location 2B where the distal end of the second conductor 3 is connected with the tubular or sleeve-like pacing electrode or pole 5. The outer diameters of coaxial convolutions of the conductors 3 and 4 are at least substantially identical and these conductors are insulated from each other, e.g., by providing an insulating layer or coat for the convolutions of the conductor 4. The insulator 9 surrounds the conductors 3, 4 and is surrounded by the fourth conductor 7 which, in turn, is surrounded by a tubular sheath-like insulator 12. The latter is surrounded by the electrode 5. The distal end portion 3a of the conductor 3 is bare and extends outwardly through an opening of the insulator 9 as well as through an opening 7B of the conductor 7 to be welded or soldered to the external surface of the conductor 7.

The connection of FIG. 6 further comprises at least one band 6 having a first portion 6b which is welded or soldered a second portion 6a which is welded or soldered to the external surface of the conductor 7, and an S-shaped or Z-shaped intermediate portion 6c which extends through the insulator 12. The illustrated welded or soldered joint 13 is adjacent the distal (second) end 14 of the electrode 5.

All embodiments of the connection between a tubular pacing electrode (5 or 5′) and the corresponding conductor (3 or 3′) exhibit the advantage that they are highly reliable because they do not rely on mere frictional contact or clamping engagement between neighboring current conducting parts. Moreover, the connections are capable of standing pronounced tensional stresses without damage thereto. The connections can employ soldered joints if the materials to be electrically connected to each other are different and if it is desired to ensure the establishment of a highly conductive connection. Welded joints can be used if the material of the band or bands 6 or 6′ is the same as that of the electrode 5 or 5′ and conductor 7 or 7′. An advantage of joints 13 which are adjacent the distal ends of the respective electrodes or poles 5 or 5′ is that such joints can be formed with ease even though the portions 6b or 6b′ of the bands 6 or 6′ are adjacent the internal surfaces of the respective electrodes 5 or 5′. The welded or soldered joints 3a between the band or bands 6 or 6′ and the tubular conductor 7 or 7′ can be formed as soon as the conductor 7 or 7′ is installed at the location 2, 2A, 2B or 2′ or even prior to mounting of the conductor 7 or 7′ at such location. This is due to the fact that the portion 6a or 6a′ of each band 6 or 6′ is welded or soldered to the external surface of the respective conductor 7 or 7′.

The provision of a welded or soldered joint between the distal end portion of the conductor 3 or 3′ and the conductor 7 or 7′ constitutes a desirable and advantageous feature of the improved electrical connection. Thus, the connection can be formed in such a way that all of its parts are positively connected (bonded) to each other. This enhances the reliability of the electrical connection and contributes to its mechanical strength. Thus, the connection between an electrode 5 or 5′ and the corresponding conductor 3 or 3′ need not rely on mere friction and/or on mere clamping action. This is important in cardiac pacemaker leads because the electrodes are in constant motion as soon as they are implanted in the heart of a patient.

The band or bands 6 and 6′ exhibit the advantage that they are stronger than wires and are just as flexible in the desired direction or directions. The intermediate portions 6c, 6c′ of such bands ensure that the respective electrodes 5 or 5′ have a certain freedom of axial movement relative to the distal ends of the respective conductors 3, 3′ without the danger of an interruption of the electrical connection between such parts. Such movability of the electrode 5 or 5′ is highly desirable when the electrode is implanted in and is maintained in constant motion by the heart of a patient or is subjected to dynamic stresses by a carrier or for any other reason.

An additional advantage of the band or bands 6, 6′ is that the width of such band or bands can be increased (in order to enhance the strength) without affecting the movability of the respective tubular pacing electrode and of the associated wire-like conductor 3 or 3′ in the desired directions, mainly axially of the tubular electrode. In addition, an electrical connection (such as the joints 13 and/or 13a) between a relatively wide band and a tubular electrode (5 or 5′) or a tubular conductor (7 or 7′) is more reliable than that between a tubular electrode and/or tubular conductor on the one hand and a thin wire on the other hand. Still further, a relatively wide band is less likely to be sheared off by an adjacent tubular electrode or tubular conductor than a relatively thin wire. The flexibility of the band is compounded by the S-shaped or Z-shaped intermediate portion to thus ensure that the electrode 5 or 5′ can perform all necessary movements relative to the corresponding conductor 3 or 3′ without risking damage to the electrical connection, even after long periods of use. It has been found that the intermediate portions 6c, 6c′ can reliably prevent the development of undesirable or excessive tensional stresses when the electrode 5 or 5′ is in constant motion subsequent to implantation in the heart of a patient. The intermediate portions 6c, 6c′ prevent the development of pronounced tensional stresses in the bands themselves as well as in the joints between these bands and the electrodes 5, 5′ and/or tubular conductors 7, 7′.

Though it is possible to omit the tubular conductor 7 or 7′, i.e., to bond the portion 6a or 6a′ of the band 6 or 6′ directly to the distal convolutions of the conductor 3 or 3′, the provision of a tubular conductor 7 or 7′ is preferred at this time because such conductor contributes significantly to reliability of the electrical connection between the conductor 3 or 3′ and the respective electrode or pole 5 or 5′.

The extent of thermally induced expansion or contraction of the conductor 7 or 7′ need not match the extent of thermally induced expansion or contraction of the associated electrode 5 or 5′. The reason is that the band or bands 6, 6′ can fully compensate for eventual differences between the thermally induced expansion or contraction of the parts 3, 5 or 3′, 5′.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A cardiac pacemaker lead having a proximal end and a distal end and comprising a first pacing electrode at said distal end; a second pacing electrode between said first electrode and said proximal end; a first elongated conductor connected to said first electrode and extending toward said proximal end; a second elongated conductor insulated from said first conductor and extending from said second electrode toward said proximal end; at least one substantially band-shaped third conductor; and means for positively connecting said at least one third conductor to said second conductor, said connecting means comprising a tubular fourth conductor positively connected with said at least one third conductor, one of said fourth conductor and said second electrode surrounding the other of said fourth conductor and said second electrode.

2. The lead of claim 1, further comprising a tubular insulator surrounding said first and second conductors and being surrounded by said second electrode.

3. The lead of claim 1, wherein at least one of said first and second conductors is a helically wound wire.

4. The lead of claim 1, wherein said third conductor includes a first elongated portion contacting said second electrode, a second elongated portion contacting said fourth electrode and a substantially Z-shaped or S-shaped intermediate portion between said first and second portions.

5. The lead of claim 4, wherein at least one of said first and second portions extends substantially axially of said second electrode and said fourth conductor.

6. The lead of claim 1, wherein said second electrode has a first length and said tubular fourth conductor has a second length which equals or approximates said first length.

7. The lead of claim 6, further comprising a tubular insulator surrounding said conductors and being surrounded by said second electrode, said second electrode being a press fit on said tubular insulator.

8. The lead of claim 1, wherein each of said first and second conductors is a helically wound wire and said second conductor coaxially surrounds said first conductor, and further comprising a tubular first insulator between (a) said first and second conductors and (b) said second electrode, and a second tubular insulator between said first and second conductors, said fourth conductor being disposed between said second insulator and said second conductor, said at least one third conductor having a first portion connected with an internal surface of said second electrode, a second portion contacting said fourth conductor and an intermediate portion contacting said second conductor and extending substantially transversely of and through said second conductor and said first insulator.

9. The lead of claim 8, wherein said second conductor comprises a plurality of neighboring convolutions and the intermediate portion of said at least one third conductor contacts at least two of said convolutions.

10. The lead of claim 9, wherein said first and second conductors are helically wound wires with convolutions which are electrically insulated from each other and have a common axis and at least substantially identical outer diameters, said fourth conductor being confined in said first and second conductors.

11. The lead of claim 10, wherein said at least one third conductor is electrically connected to an external surface of said fourth conductor and includes a portion disposed between said convolutions.

12. The lead of claim 10, further comprising a tubular insulator between said fourth conductor and said helically wound wires, said second conductor having an end portion extending through an opening of said tubular insulator and connected with said fourth conductor, said at least one third conductor having a first portion connected to said second electrode, a second portion connected to an external surface of said fourth conductor and an intermediate portion extending between said first and second portions through said insulator and between said convolutions.

13. The lead of claim 12, wherein said first portion is connected to an internal surface of said second electrode.

14. The lead of claim 1, wherein said connecting means comprises at least one welded or soldered joint.

15. The lead of claim 1, wherein said second electrode has a first end and a second end between said first end and said first electrode, said connecting means comprising a welded or soldered joint connecting said second end with said at least one third conductor.

16. The lead of claim 1, further comprising a tubular third electrode adjacent said second electrode, a further conductor extending from said third electrode toward said proximal end, and means for electrically connecting said further conductor with said third electrode.

17. The lead of claim 16, wherein said means for electrically connecting said further conductor with said third electrode comprises a tubular conductor surrounded by said third electrode and connected with said further conductor and at least one substantially band-like conductor connecting said third electrode with said tubular conductor.

18. A cardiac pacemaker lead having a proximal end and a distal end and comprising a first pacing electrode at said distal end; a second pacing electrode between said fist electrode and said proximal end; a first elongated conductor connected to said first electrode and extending toward said proximal end; a second elongated conductor insulated from said first conductor and extending from said second electrode toward said proximal end, each of said first and second conductors constituting a helically wound wire with convolutions having common axes and at least substantially identical outer diameters; at least one substantially band-shaped third conductor; means for positively connecting said at least one third conductor to said second electrode nd to said second conductor, including a tubular fourth conductor surrounding said wires and being surrounded by said second electrode; a first tubular insulator surrounding said wires and surrounded by said fourth conductor; and a second tubular insulator disposed between said second conductor having an end portion extending through said first insulator and connected to an external surface of said fourth conductor, said at least one third conductor being connected to said external surface and extending through said second insulator.

19. The lead of claim 18, wherein said second electrode has an internal surface which is connected with said at least one third conductor.

20. A cardiac pacemaker lead having a proximal end and a distal end and comprising a first pacing electrode at said distal end; a second pacing electrode between said first electrode and said proximal end; a first elongated conductor connected to said first electrode and extending toward said proximal end; a second elongated conductor insulated from said first conductor and extending from said second electrode toward said proximal end; at least one substantially band-shaped third conductor; and means for positively connecting said at least one third conductor to said second electrode and to said second conductor, including a tubular fourth conductor surrounded by said second electrode and electrically connected with said second conductor and at lest one welded or soldered joint connecting said at least one third conductor with said fourth conductor.

21. A cardiac pacemaker lead having a proximal end and a distal end and comprising a first pacing electrode at said distal end; a second pacing electrode between said first electrode and said proximal end; a first elongated conductor connected to said first electrode and extending toward said proximal end; a second elongated conductor insulted from said first conductor and extending from said second electrode toward said proximal end; at least one substantially band-shaped third conductor; and means for positively connecting said at least one third conductor to said second electrode and to said second conductor, including a tubular fourth conductor surrounded by said second electrode and connected with said at least one third conductor, said second conductor having an end portion which is welded or soldered to said fourth conductor.

* * * * *